US005294535A

United States Patent [19]
Gribnau et al.

[11] Patent Number: 5,294,535
[45] Date of Patent: Mar. 15, 1994

[54] METHOD FOR SUPPRESSING PARTIAL COLORATION IN IMMUNOASSAYS UTILIZING PEROXIDASE LABELS

[75] Inventors: Thomas C. J. Gribnau, Heesch; Leonardus P. C. Kupers, Teeffelen; Petrus A. L. Goossens, Oss, all of Netherlands

[73] Assignee: Akzo N.V., Arnhem, Netherlands

[21] Appl. No.: 944,760

[22] Filed: Sep. 14, 1992

Related U.S. Application Data

[63] Continuation-in-part of Ser. No. 627,570, Dec. 11, 1990, abandoned, which is a continuation of Ser. No. 334,020, Apr. 5, 1989, abandoned.

[30] Foreign Application Priority Data

Apr. 6, 1988 [NL] Netherlands ............... 88.00874

[51] Int. Cl.$^5$ .............. C12N 9/96; C12Q 1/28; G01N 33/535
[52] U.S. Cl. ...................... 435/7.9; 435/28; 435/188; 435/810; 435/962; 436/175; 436/825; 436/826
[58] Field of Search ............... 435/7.9, 28, 188, 810, 435/962; 436/826, 825, 175

[56] References Cited

U.S. PATENT DOCUMENTS

| | | | |
|---|---|---|---|
| 4,454,232 | 6/1984 | Breglio et al. | 436/504 |
| 4,596,770 | 6/1986 | Parham et al. | 435/7.9 |
| 4,810,642 | 3/1989 | Aoyama et al. | 435/28 |

FOREIGN PATENT DOCUMENTS

| | | |
|---|---|---|
| 0121317 | 10/1984 | European Pat. Off. |
| 0177244 | 4/1986 | European Pat. Off. |
| 0187862 | 11/1983 | Japan |

OTHER PUBLICATIONS

Heath, R. L. et al., "A New Sensitive Assay for the Measurement of Hydro-perosidase," Analytical Biochem. 76, pp. 184–192 (1976), USA.

Porstmann, B., "Comparison of Chromogens for the Determination of Horseradish Peroxidase as a Marker in Enzyme Immunoassay," J. Clin. Chem. Clin. Biochem., vol. 19, 1981, pp. 435–439, USA.

Voller et al., Enzyme Imunoassays, Chap. 6, Alternative Immunoassays, Ed. W. P. Collins, 1985, pp. 77–86.

*Primary Examiner*—Esther L. Kepplinger
*Assistant Examiner*—Nancy J. Parsons
*Attorney, Agent, or Firm*—Donna Bobrowicz; Mary E. Gormley

[57] ABSTRACT

The invention concerns a method for detecting an analyte in a blood sample or a derived fraction thereof. In this method one uses the binding affinity between the analyte and its specific binding agent. Moreover, a reaction component containing a peroxidase label is added to the sample and specific binding agent to form a reaction mixture. The incubation of the reaction mixture, containing the analyte and its specific binding agent, with the peroxidase-labeled reaction component has to be carried out in the presence of a quaternary ammonium salt or ionic surfactant.

2 Claims, No Drawings

METHOD FOR SUPPRESSING PARTIAL COLORATION IN IMMUNOASSAYS UTILIZING PEROXIDASE LABELS

This is a continuation-in-part of application Ser. No. 07/627,570 filed Dec. 11, 1990, now abandoned, which is a file wrapper continuation of U.S. Ser. No. 07/334,020, filed Apr. 5, 1989, now abandoned.

BACKGROUND OF THE INVENTION

The invention relates to a method for quantitatively and/or qualitatively detecting a specific binding substance in blood or a derived fraction thereof using the binding affinity between the specific binding substance and its co-reactant. Moreover a reaction component with peroxidase activity has been used by incubating a reaction mixture containing the specific binding substance and its co-reactant and by which the peroxidase activity in said reaction mixture or a fraction derived therefrom has been determined. The peroxidase activity is a measure of the quantity and/or presence of the specific binding substance. Also a test kit for carrying out said method is part of the invention. Such a method to demonstrate a peroxidase activity has already been described in Dutch Patent 154,600.

As carrier material in said method has often been used the wall of a small well in a microtitration plate to which antibodies are bonded. The blood to be investigated or a fraction derived therefrom, such as serum, is introduced into the small wells of the microtitration plate. The bonded antibody is able to react with the antigen present in the blood or a derived fraction thereof, as a result of which said antigen is bonded. In order to be able to detect whether an immunochemical reaction has taken place, subsequently one can use marked antibodies which are directed against the antigen to be determined. Said marked antibodies will react with the antibody-antigen complex formed already on the solid phase. The marked antibodies consist of antibodies to which an enzyme is bonded, preferably a peroxidase-enzyme. In the next step, a colourless solution (substrate+chromogen) is added. The enzyme is able to convert this solution into a coloured compound. The intensity of the colour depends on the quantity of enzyme which is proportional to the quantity of bound antigen. Said colour can be altered by adding a stop reagent. The method thus described of determining an antigen in blood or a derived fraction thereof is a method of the sandwich type. Other immunochemical methods, such as an inhibition reaction and a competition reaction, can also be used. As suitable enzymes one can use, inter alia, alkaline phosphatase, urease and a previously mentioned peroxidase, preferably Horse Radish Peroxidase (HRP). The HRP catalyses the conversion of the substrate, a peroxide compound, in water. The electrons needed for this reaction may be supplied by chromogenic substances such as tetramethylbenzidine (TMB). The TMB is converted as a result into coloured complexes, by which the enzyme action is demonstrated. The colour formed can either be detected visually or the enzyme action can be determined in an analytically suitable manner.

In examining blood for the presence of antigens or antibodies, it is usual that the serum containing the antigens or antibodies to be determined has been separated from the blood cells prior to the determination.

In practice it emerges that an undesired, increased colour intensity is often produced, in particular in carrying out an enzyme immunoassay (EIA) when a peroxidase being used as enzyme. This phenomenon is also described as partial coloration.

It will be clear that this phenomenon of partial coloration will lead to undesired results and conclusions. In this connection one can mention so-called AIDS antibody tests. In these tests sera of blood donors are tested routinely in an enzyme immunoassay for the presence of antibodies directed against the AIDS virus.

BRIEF SUMMARY OF THE INVENTION

The present invention is therefore characterized in that the determination of the peroxidase activity is carried out in the presence of ionic surfactants, and particularly a quaternary ammonium salt. These ionic surfactants effectively and surprisingly suppress partial coloration during the course of immunological testing where enzyme labels with peroxide activity are used, and especially with the use of substrates for example, TMB (tetramethylbenzidine), which are converted by peroxides in a color reaction.

These substrates can give an undesired color reaction with certain blood components, such as erythrocytes and hemoglobin. These components may give a false positive test result in an immunological test where enzyme labels with peroxide activity or substrates as described above are used.

DETAILED DESCRIPTION OF THE INVENTION

A number of different ionic surfactants useful in this invention include quaternary ammonium salts, cationics or anionics.

As quaternary ammonium salts one can use for example dodecyltrimethylammonium bromide, hexadecyltrimethylammonium bromide, tetradecyltrimethylammonium bromide, alkyldimethylbenzylammonium chloride, benzethonium chloride, benzyldimethylhexadecylammonium chloride, cetyldimethylethylammonium bromide, cetylpyridinium bromide, cetylpyridinium chloride, dimethyldioctadecylammonium bromide and methylbenzethonium chloride. As preference for suitable quaternary ammonium salts, use is made of dodecyltrimethylammonium bromide (DTAB), hexadecyltrimethylammonium bromide (CTAB) or alkyldimethylbenzylammonium chloride (benzalkonium chloride). Optionally, other detergents and, in particular, cationic detergents such as quaternary phosphonium salts or anionic detergents such as N-lauroylsarcosine, sodium lauryl sulphate or sodium dodecyl sulphate can also be used.

It is surprising that the peroxidase activity can be determined by adding these ionic surfactants, and in particular, these said quaternary ammonium salts, with the partial coloration being significantly suppressed. If desired, whole blood can be used diluted or undiluted as a sample, the red blood cells being removed as well as possible before determining the peroxidase activity. Quaternary ammonium salt can be added to the test in the form of a solution containing the quaternary ammonium salt or as a solid compound.

This addition of the ionic surfactant to the test may be carried out either together with the substrate, or together with the chromogen, or together with a substrate/chromogen mixture.

The invention also relates to a test kit which contains the components such as a peroxidase-enzyme-conjugate and a quaternary ammonium salt for carrying out the method according to the invention.

The method according to the invention for quantitatively and/or qualitatively detecting a specific binding substance in blood or a derived fraction thereof can be carried out in any reaction in which the binding of the specifically binding substance with its co-reactant is determined by using a reaction component having peroxidase activity. The determination of the peroxidase activity is a measure of the quantity and/or presence of the specifically binding substance.

Thus, one can use, for example, the previously mentioned sandwich—but also an inhibition—or competition reaction.

A "specifically binding substance" may be understood to mean for example a hapten, an antigen or a fragment thereof, an antibody or a fragment thereof or protein A, DNA or RNA.

"Its co-reactant" may be understood to mean for example, a hapten, an antigen or a fragment thereof, an antibody or a fragment thereof or protein A, DNA or RNA, said co-reactant having a binding affinity for the specifically binding substance. This co-reactant may optionally be bound to carrier material.

A "reaction component" may be understood to mean for example, a hapten, an antigen or a fragment thereof, an antibody or a fragment thereof or protein A, DNA or RNA, by which said reaction component also has peroxidase activity, which component does not need to be bound to a solid carrier and which component can be used in solid form, in freeze-dried form or in solution.

If the antigen is detected in the method according to the invention with the aid of a sandwich reaction, said antigen can be incubated with a carrier material to which antibodies which are directed against the antigen to be determined have already been bound. As carrier one may use for example test tubes, microtitration plates, rods, beads or discs made of, for example, glass or plastic. The detection of whether complex formation has occurred between the antibody bound to the solid carrier and the antigen to be determined is carried out by subsequently adding a second antibody provided with an enzyme.

The enzyme is selected, inter alia, on the basis of reactivity and stability. Enzymes such as alkaline phosphatase, urease, glucose oxidase, galactose oxidase and peroxidase enjoy preference, in particular the group of the peroxidases. Said enzymes are capable of catalysing a conversion of a peroxide-substrate, in which coloured components are involved. Within this group, HRP enzyme has a pronounced preference owing, primarily, to good stability and low cost price. The electron-supplying substances also needed for said enzyme reaction may, for example, be chromogens. Suitable chromogens are, for example, tetramethylbenzidine, o-phenylenediamine, 5-aminosalicylic acid, 2,2'-azino-di-[3-ethylbenzothiazoline-6-sulphonate], the preference being for tetramethylbenzidine (TMB). Said TMB is converted during the reaction into coloured complexes, as a result of which the enzyme action is detected, and this provides a qualitative and/or quantitative measure of the antigen to be determined.

The invention is explained further with reference to the following examples.

EXAMPLE I

Detection of HBsAg (Hepatitis B Surface Antigen) in serum

A serum pool which was negative for HBsAg was examined.

A. Reagents

1. Coated microtitration plates

The small wells of polystyrene microtitration plates were coated on the inside with a monoclonal antibody directed against HBsAg by a method known in immunochemistry.

2. Conjugate

A conjugate of antibodies directed against HBsAg and horse radish peroxidase (HRP) was prepared according to a method which is conventional in immunochemistry.

3. Substrate/chromogen

As substrate, use was made of a urea peroxidase solution, while as chromogen, use was made of a TMB solution (tetramethylbenzidine dissolved in dimethyl sulphoxide). The substrate/chromogen solution was divided into two equal parts. To one part a quaternary ammonium salt (CTAB) was added in a concentration of 0.2 g/l (group A), while no quaternary ammonium salt was introduced into the other part (group B).

B. Performance of the Test

The coated microtitration plates were incubated for 30 minutes at 50° C. with 0.1 ml of the serum to be examined in the respective small wells.

Subsequently the small wells were drained and washed 4 times with a washing buffer (PBS/Tween ®) and drained again.

0.1 ml of the conjugate was subsequently introduced into each of the small wells. After an incubation for 30 minutes at 50° C., the small wells were again drained, washed and drained.

Subsequently the microtitration plates were divided into two groups: group A and group B. The small wells in the plates belonging to group A then received 0.1 ml of substrate/chromogen mixture together with the CTAB. The small wells in the plates belonging to group B received the substrate/chromogen mixture to which no CTAB had been added.

After incubating for 30 minutes at 25° C., the enzyme reaction was stopped by adding 0.1 ml of sulphuric acid solution (2M) to each small well.

C. Results

The results obtained from both groups are shown in the table.

TABLE

|  | CTAB added (group A) | CTAB not added (group B) |
|---|---|---|
| Exp. 1 | | |
| number of small wells tested | 320 | 320 |
| number of small wells in which partial coloration was detected | 9 | 20 |
| Exp. 2 | | |
| number of small wells tested | 320 | 320 |
| number of small wells in which partian coloration was detected | 16 | 51 |

EXAMPLE II

The Effect of CTAB on the Reaction of HRP and Erythrocytes with a Substrate of Ureaperoxide and Tetramethylbenzidine

Materials and Methods

Samples:
HRP and chimp erythrocytes were diluted in saline.
Substrate:
Ureaperoxide and tetramethylbenzidine were dissolved in concentrations and in a buffer optimal for conversion by HRP, and contained various concentrations of CTAB.
Test performance:
In the wells of a microplate, 50 μl of sample was mixed with 100 μl of substrate and the mixture was incubated for 30 minutes at 18°–25° C. The reaction was stopped by adding 100 μl of 1 mol/l $H_2SO_4$ and the absorbencies read spectrophotometrically at 450 nm.
Results:

|  | ABSORBANCE | | | | | | | | |
|---|---|---|---|---|---|---|---|---|---|
| CTAB Concentr. | HRP (ng/ml) | | | | | Erythrocytes (concentrations relative to whole blood) | | | |
| | 2 | 1 | 0.5 | 0.25 | 0 | 1/10000 | 1/20000 | 1/40000 | 1/80000 | Blank |
| 0 | 1.67 | 0.88 | 0.43 | 0.23 | 0.03 | 2.99 | 2.89 | 1.79 | 0.88 | 0.03 |
| 0.1 g/l | 2.02 | 1.10 | 0.59 | 0.30 | 0.05 | 0.46 | 0.25 | 0.15 | 0.10 | 0.05 |
| 0.2 g/l | 1.91 | 1.04 | 0.55 | 0.29 | 0.05 | 0.38 | 0.21 | 0.13 | 0.09 | 0.05 |
| 0.4 g/l | 1.65 | 0.90 | 0.49 | 0.26 | 0.05 | 0.31 | 0.19 | 0.12 | 0.10 | 0.05 |

Conclusion:

CTAB in concentrations of 0.1 up to 0.4 g/l barely influences the reactivity of the substrate with HRP, whereas it considerably inhibits the reactivity with erythrocytes. As seen here, the reactivity with erythrocytes is inhibited by greater than 50% in all cases, and in some cases, greater than 90% (0.4 g/l CTAB with 1/10,000 RBC concentration.)

EXAMPLE III

Effect of CTAB on the Reaction of Hemoglobin with a Substrate of Urea, Peroxide and Tetramethylbenzidine

Materials and Methods

Tests were performed analogously to Example II, however, 10 μl volumes of hemoglobin in 9 g/l NaCl were used as samples.
Results:

| CTAB (g/l) | ABSORBANCE Hemoglobin (μg/ml) | | | | |
|---|---|---|---|---|---|
| | 330 | 100 | 33 | 10 | 0 |
| 0 | >2.00 | >2.00 | 1.24 | 0.24 | 0.03 |
| 0.1 | 1.22 | 0.34 | 0.13 | 0.07 | 0.05 |
| 0.2 | 1.00 | 0.28 | 0.11 | 0.07 | 0.05 |
| 0.4 | 0.79 | 0.23 | 0.10 | 0.07 | 0.05 |

Conclusion:
CTAB considerably inhibits the reactivity of hemoglobin with the substrate.

EXAMPLE IV

Effect of Various detergents on the Reaction of HRP and Erythrocytes with a Substrate of Ureaperoxide and Tetramethylbenzidine

Materials and Methods

Tests were performed analogously to Example II. However, equivalents of 50 μl sample were added to 100 μl of substrate containing the indicated concentrations of detergent.

Results:

| Detergent (g/l) | HRP (ng/ml) | | | Blank | ERYTHROCYTES | | |
|---|---|---|---|---|---|---|---|
| | 2 | 1 | 0.5 | | 1/500 | 1/5000 | 1/50000 |
| None | 1.46 | 0.68 | 0.40 | 0.03 | >2.00 | >2.00 | 1.47 |
| SDS (0.05) | >2.00 | 1.25 | 0.80 | 0.13 | 0.68 | 0.43 | 0.23 |
| N-Lauroyl Sarcosine (0.1) | 1.71 | 1.12 | 0.70 | 0.17 | 0.70 | 0.80 | 0.27 |
| DTAB (4.0) | 1.74 | 0.83 | 0.49 | 0.05 | 0.57 | 0.76 | 0.12 |
| CTAB (1.0) | 1.20 | 0.60 | 0.34 | 0.05 | 0.46 | 0.46 | 0.10 |
| CTAB (0.33) | 1.51 | 0.80 | 0.46 | — | 1.49 | 0.84 | 0.12 |

Conclusion:
SDS, N-lauroyl sarcosine, DTAB and CTAB strongly inhibit the reaction of erythrocytes with the substrate, whereas there is a very minimal affect, and an occasional increase, in the reactions of HRP.

We claim:

1. In an enzyme immunoassay that quantitatively and/or qualitatively detects, through the measurement of a peroxidase label, an analyte in a blood sample or a fraction thereof, comprising contacting the blood sample with reagents comprising specific binding agents for the analyte and a peroxidase label conjugated to one of said reagents, in a reaction mixture to form an immune complex, and thereafter detecting the presence or amount of analyte by determining the extent of the peroxidase activity in said reaction mixture, by incubating the peroxidase-label with a peroxidase-substrate/-chromogen mixture, wherein the improvement comprises carrying out said incubating step in the presence of a quaternary ammonium salt, wherein said quaternary ammonium salt is present in an amount sufficient to suppress partial coloration at least 50% over that of said enzyme immunoassays not containing the quaternary ammonium salt.

2. In an enzyme immunoassay that quantitatively and/or qualitatively detects, through the measurement of a peroxidase label, an analyte in a blood sample or a fraction thereof, comprising contacting the blood sample with reagents comprising specific binding agents for the analyte and a peroxidase label conjugated to one of said reagents, in a reaction mixture to form an immune complex, and thereafter detecting the presence or amount of analyte by determining the extent of the peroxidase activity in said reaction mixture, by incubating the peroxidase label with a peroxidase-substrate/chromogen mixture, wherein the improvement comprises carrying out said incubating step in the presence of a cationic or anionic surfactant, wherein said surfactant is present in an amount sufficient to suppress partial coloration at least 50% over that of said enzyme immunoassays not containing the surfactant.

* * * * *